US011896693B2

(12) United States Patent
Zhao et al.

(10) Patent No.: US 11,896,693 B2
(45) Date of Patent: *Feb. 13, 2024

(54) HAIR CONDITIONER COMPOSITIONS WITH A PRESERVATIVE SYSTEM CONTAINING SODIUM BENZOATE AND GLYCOLS AND/OR GLYCERYL ESTERS

(71) Applicant: The Procter & Gamble Company, Cincinnati, OH (US)

(72) Inventors: Jean Jianqun Zhao, Cincinnati, OH (US); Heather Lynn Focht, Lebanon, OH (US); David Joseph Kaufman, Fairfield, OH (US); Deborah Mulligan, Cincinnati, OH (US); Lina Aurora Witte, Monroe, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/108,090

(22) Filed: Dec. 1, 2020

(65) Prior Publication Data

US 2021/0161780 A1 Jun. 3, 2021

Related U.S. Application Data

(60) Provisional application No. 62/942,209, filed on Dec. 2, 2019, provisional application No. 62/942,208, filed on Dec. 1, 2019.

(51) Int. Cl.
| | |
|---|---|
| *A61K 8/34* | (2006.01) |
| *A61K 8/04* | (2006.01) |
| *A61Q 5/12* | (2006.01) |
| *A61K 8/368* | (2006.01) |
| *A61K 8/37* | (2006.01) |
| *A61K 8/41* | (2006.01) |
| *A61K 8/19* | (2006.01) |
| *A61K 8/20* | (2006.01) |
| *A61K 8/36* | (2006.01) |
| *A61K 8/42* | (2006.01) |

(52) U.S. Cl.
CPC ............ *A61K 8/345* (2013.01); *A61K 8/042* (2013.01); *A61K 8/19* (2013.01); *A61K 8/20* (2013.01); *A61K 8/342* (2013.01); *A61K 8/36* (2013.01); *A61K 8/368* (2013.01); *A61K 8/375* (2013.01); *A61K 8/416* (2013.01); *A61K 8/42* (2013.01); *A61Q 5/12* (2013.01); *A61K 2800/30* (2013.01); *A61K 2800/34* (2013.01); *A61K 2800/524* (2013.01)

(58) Field of Classification Search
CPC . A61K 9/107; A61K 8/92; A61Q 5/00; A61Q 5/12; A61P 31/04
See application file for complete search history.

(56) References Cited

U.S. PATENT DOCUMENTS

| | | | |
|---|---|---|---|
| 2,356,168 | A | 8/1944 | Mabley |
| 2,396,278 | A | 3/1946 | Otto |
| 2,438,091 | A | 3/1948 | Lynch |
| 2,486,921 | A | 11/1949 | Byerly |
| 2,486,922 | A | 11/1949 | Bruce |
| 2,528,378 | A | 10/1950 | Mannheimer |
| 2,613,185 | A | 10/1952 | Marshall |
| 2,658,072 | A | 11/1953 | Milton |
| 2,694,668 | A | 11/1954 | Fricke |
| 2,809,971 | A | 10/1957 | Jack et al. |
| 3,152,046 | A | 10/1964 | Maria |
| 3,236,733 | A | 2/1966 | Karsten et al. |
| 3,321,425 | A | 5/1967 | Karl-ludwig et al. |
| 3,332,880 | A | 7/1967 | Adriaan et al. |
| 3,426,440 | A | 2/1969 | Shen et al. |
| 3,463,308 | A | 8/1969 | Deneke |
| 3,489,688 | A | 1/1970 | Pospischil |
| 3,653,383 | A | 4/1972 | Wise |
| 3,695,989 | A | 10/1972 | Albert |
| 3,753,196 | A | 8/1973 | Kurtz et al. |
| 3,761,418 | A | 9/1973 | Parran |
| 3,929,678 | A | 12/1975 | Laughlin |
| 3,967,921 | A | 7/1976 | Haberli et al. |
| 4,020,156 | A | 4/1977 | Murray et al. |
| 4,051,081 | A | 9/1977 | Jabs et al. |
| 4,089,945 | A | 5/1978 | Brinkman et al. |

(Continued)

FOREIGN PATENT DOCUMENTS

| | | |
|---|---|---|
| CN | 1138091 | 12/1996 |
| CN | 1219388 | 6/1999 |

(Continued)

OTHER PUBLICATIONS

VegeCide. https://web.archive.org/web/20120824144807/http://www.ingredientstodiefor.com/item/VegeCide/925/. Published: Aug. 24, 2012.*
PCT Search Report and Written Opinion for PCT/US2020/062656 dated Mar. 12, 2021.
All Office Actions, U.S. Appl. No. 16/953,975.
All Office Actions, U.S. Appl. No. 17/108,081.
All Office Actions, U.S. Appl. No. 17/209,292.
Anonymous "P8136 Poly(vinyl alcohol)" Internet article, [Online] XP002538935 retrieved from the Internet: URL:hllp/20NWW.sigmaaldrich.com/catalog/ProductDetail.do?D7=0%N25-SEARCH_CONCAT PNOIDBRAND KEY%N4=P8136%7SCIAL%N25=0%QS=ON%F=SPEC retrieved on Jul. 28, 2009.

(Continued)

*Primary Examiner* — Robert T. Crow
*Assistant Examiner* — John P Nguyen
(74) *Attorney, Agent, or Firm* — John G. Powell; Alexandra S Anoff (57) ABSTRACT

A hair conditioner composition containing an aqueous carrier, a cationic surfactant, a high melting point fatty compound and an effective preservation system. The conditioner composition comprises a gel network. The preservation system contains sodium benzoate and a second composition selected from the group consisting of glycol, glyceryl ester, and combinations thereof.

13 Claims, 1 Drawing Sheet

(56) References Cited

U.S. PATENT DOCUMENTS

| | | |
|---|---|---|
| 4,149,551 A | 4/1979 | Benjamin et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,663,158 A | 5/1987 | Wolfram et al. |
| 4,710,374 A | 12/1987 | Grollier et al. |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,476,597 A | 12/1995 | Sakata et al. |
| 5,501,238 A | 3/1996 | Borstel et al. |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| 5,885,561 A | 3/1999 | Flemming et al. |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. et al. |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D442,739 S | 5/2001 | Friesenhahn |
| D443,389 S | 6/2001 | Friesenhahn |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D484,749 S | 1/2004 | Garraway |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| D739,227 S | 9/2015 | Mitchell et al. |
| D740,928 S | 10/2015 | Bruining et al. |
| 9,198,838 B2 | 12/2015 | Glenn, Jr. |
| D769,522 S | 10/2016 | Venet |
| 9,539,444 B2 | 1/2017 | Kinoshita et al. |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| 10,226,404 B2 | 3/2019 | Takahashi et al. |
| 10,278,915 B1 | 5/2019 | Kawa |
| 10,294,586 B2 | 5/2019 | Sivik et al. |
| D851,344 S | 6/2019 | Carlson et al. |
| D857,156 S | 8/2019 | Hani |
| 10,391,046 B2 | 8/2019 | Hartnett et al. |
| 10,413,496 B2 | 9/2019 | Pistorio et al. |
| D862,020 S | 10/2019 | Gorrell et al. |
| 10,449,131 B2 | 10/2019 | Li et al. |
| D866,893 S | 11/2019 | Hunt et al. |
| D867,717 S | 11/2019 | Chavez |
| D868,953 S | 12/2019 | Mckendree |
| 10,569,286 B2 | 2/2020 | Anderson et al. |
| 10,694,917 B2 | 6/2020 | Dreher et al. |

(56) References Cited

U.S. PATENT DOCUMENTS

| | | | |
|---|---|---|---|
| D910,434 S | 2/2021 | Tan et al. | |
| D910,457 S | 2/2021 | Lee | |
| 2002/0077264 A1 | 6/2002 | Roberts et al. | |
| 2002/0081930 A1 | 6/2002 | Jackson et al. | |
| 2002/0098994 A1 | 7/2002 | Zafar | |
| 2002/0099109 A1 | 7/2002 | Dufton et al. | |
| 2002/0177621 A1 | 11/2002 | Hanada et al. | |
| 2002/0187181 A1 | 12/2002 | Godbey et al. | |
| 2003/0018242 A1 | 1/2003 | Hursh et al. | |
| 2003/0032573 A1 | 2/2003 | Tanner et al. | |
| 2003/0045441 A1 | 3/2003 | Hsu et al. | |
| 2003/0069154 A1 | 4/2003 | Hsu et al. | |
| 2003/0080150 A1 | 5/2003 | Cowan | |
| 2003/0082129 A1 | 5/2003 | Buckingham et al. | |
| 2003/0099691 A1 | 5/2003 | Lydzinski et al. | |
| 2003/0099692 A1 | 5/2003 | Lydzinski et al. | |
| 2003/0180242 A1 | 9/2003 | Eccard et al. | |
| 2003/0186826 A1 | 10/2003 | Eccard et al. | |
| 2003/0194416 A1 | 10/2003 | Shefer | |
| 2003/0199412 A1 | 10/2003 | Gupta | |
| 2003/0209166 A1 | 11/2003 | Vanmaele et al. | |
| 2003/0215522 A1 | 11/2003 | Johnson et al. | |
| 2003/0232183 A1 | 12/2003 | Dufton | |
| 2004/0029762 A1 | 2/2004 | Hensley | |
| 2004/0032859 A1 | 2/2004 | Miao | |
| 2004/0048759 A1 | 3/2004 | Ribble et al. | |
| 2004/0048771 A1 | 3/2004 | Mcdermott | |
| 2004/0053808 A1 | 3/2004 | Raehse et al. | |
| 2004/0059055 A1 | 3/2004 | Inada | |
| 2004/0071742 A1 | 4/2004 | Popplewell | |
| 2004/0071755 A1 | 4/2004 | Fox | |
| 2004/0108615 A1 | 6/2004 | Foley | |
| 2004/0110656 A1 | 6/2004 | Casey et al. | |
| 2004/0115155 A1 | 6/2004 | Salvador et al. | |
| 2004/0126585 A1 | 7/2004 | Kerins et al. | |
| 2004/0175404 A1 | 9/2004 | Shefer | |
| 2004/0180597 A1 | 9/2004 | Kamada | |
| 2004/0202632 A1 | 10/2004 | Gott et al. | |
| 2004/0206270 A1 | 10/2004 | Vanmaele et al. | |
| 2004/0242097 A1 | 12/2004 | Hasenoehrl | |
| 2004/0242772 A1 | 12/2004 | Huth et al. | |
| 2005/0069575 A1 | 3/2005 | Fox | |
| 2005/0136780 A1 | 6/2005 | Clark et al. | |
| 2005/0137272 A1 | 6/2005 | Gaserod | |
| 2005/0159730 A1 | 7/2005 | Kathrani et al. | |
| 2005/0202992 A1 | 9/2005 | Grandio et al. | |
| 2005/0220745 A1 | 10/2005 | Lu | |
| 2005/0232954 A1 | 10/2005 | Yoshinari et al. | |
| 2005/0272836 A1 | 12/2005 | Yaginuma et al. | |
| 2005/0287106 A1 | 12/2005 | Legendre | |
| 2006/0002880 A1 | 1/2006 | Peffly et al. | |
| 2006/0013869 A1 | 1/2006 | Ignatious | |
| 2006/0024256 A1 | 2/2006 | Wells et al. | |
| 2006/0052263 A1 | 3/2006 | Roreger et al. | |
| 2006/0064510 A1 | 3/2006 | Low et al. | |
| 2006/0078528 A1 | 4/2006 | Yang et al. | |
| 2006/0078529 A1 | 4/2006 | Uchida et al. | |
| 2006/0128592 A1 | 6/2006 | Ross | |
| 2006/0159730 A1 | 7/2006 | Simon | |
| 2006/0228319 A1 | 10/2006 | Vona, Jr. et al. | |
| 2006/0269501 A1* | 11/2006 | Johnson | A61K 8/342 424/70.28 |
| 2006/0274263 A1 | 12/2006 | Yacktman et al. | |
| 2007/0028939 A1 | 2/2007 | Mareri et al. | |
| 2007/0031369 A1 | 2/2007 | Verboom et al. | |
| 2007/0099813 A1 | 5/2007 | Luizzi | |
| 2007/0110792 A9 | 5/2007 | Simon | |
| 2007/0135528 A1 | 6/2007 | Butler et al. | |
| 2007/0149435 A1 | 6/2007 | Koenig et al. | |
| 2007/0190005 A1* | 8/2007 | Rozsa | A61K 8/368 424/70.1 |
| 2007/0225388 A1 | 9/2007 | Cooper et al. | |
| 2007/0237736 A1 | 10/2007 | Burgo et al. | |
| 2008/0035174 A1 | 2/2008 | Aubrun-sonneville | |
| 2008/0083420 A1 | 4/2008 | Glenn et al. | |
| 2008/0090939 A1 | 4/2008 | Netravali et al. | |
| 2008/0131695 A1 | 6/2008 | Aquad et al. | |
| 2008/0138492 A1 | 6/2008 | Cingotti | |
| 2008/0139672 A1 | 6/2008 | Rozsa et al. | |
| 2008/0152894 A1 | 6/2008 | Beihoffer et al. | |
| 2008/0153730 A1 | 6/2008 | Tsaur | |
| 2008/0187507 A1* | 8/2008 | Johnson | A61Q 19/10 424/70.27 |
| 2008/0215023 A1 | 9/2008 | Scavone et al. | |
| 2008/0292669 A1 | 11/2008 | Deng et al. | |
| 2008/0293839 A1 | 11/2008 | Stobby | |
| 2009/0197787 A1 | 8/2009 | Venet et al. | |
| 2009/0232873 A1 | 9/2009 | Glenn, Jr. et al. | |
| 2009/0263342 A1 | 10/2009 | Glenn, Jr. | |
| 2010/0018641 A1 | 1/2010 | Branham | |
| 2010/0150858 A1 | 6/2010 | Runglertkriangkrai | |
| 2010/0150976 A1 | 6/2010 | Schnitzler | |
| 2010/0167971 A1 | 7/2010 | Glenn, Jr. et al. | |
| 2010/0173817 A1 | 7/2010 | Glenn, Jr. et al. | |
| 2010/0286011 A1 | 11/2010 | Glenn, Jr. et al. | |
| 2010/0291165 A1 | 11/2010 | Glenn, Jr. et al. | |
| 2011/0023240 A1 | 2/2011 | Fossum | |
| 2011/0027328 A1 | 2/2011 | Baig et al. | |
| 2011/0028374 A1 | 2/2011 | Fossum et al. | |
| 2011/0033509 A1 | 2/2011 | Simon | |
| 2011/0165110 A1 | 7/2011 | Kinoshita et al. | |
| 2011/0182956 A1 | 7/2011 | Glenn, Jr. et al. | |
| 2011/0189247 A1 | 8/2011 | Glenn, Jr. | |
| 2011/0195098 A1 | 8/2011 | Glenn, Jr. | |
| 2011/0250256 A1 | 10/2011 | Hyun-oh et al. | |
| 2011/0287687 A1 | 11/2011 | Kramer et al. | |
| 2012/0021026 A1 | 1/2012 | Glenn, Jr. | |
| 2012/0052036 A1 | 3/2012 | Glenn, Jr. | |
| 2012/0052037 A1 | 3/2012 | Sivik et al. | |
| 2012/0107534 A1 | 5/2012 | Wnuk et al. | |
| 2012/0237576 A1 | 9/2012 | Gordon | |
| 2012/0270029 A1 | 10/2012 | Glenn, Jr. et al. | |
| 2012/0294823 A1 | 11/2012 | Aramwit | |
| 2012/0321580 A1 | 12/2012 | Glenn, Jr. | |
| 2013/0236520 A1 | 9/2013 | Popovsky et al. | |
| 2013/0280193 A1 | 10/2013 | Carter et al. | |
| 2013/0303419 A1 | 11/2013 | Glenn, Jr. et al. | |
| 2014/0105942 A1 | 4/2014 | Pistorio et al. | |
| 2014/0329428 A1 | 11/2014 | Glenn, Jr. | |
| 2014/0356307 A1* | 12/2014 | Yang | A61K 8/342 424/70.28 |
| 2015/0017218 A1 | 1/2015 | Pettigrew et al. | |
| 2015/0250701 A1 | 9/2015 | Hamersky et al. | |
| 2015/0290109 A1 | 10/2015 | Simonnet et al. | |
| 2015/0297494 A1 | 10/2015 | Mao | |
| 2015/0313803 A1 | 11/2015 | Lynch et al. | |
| 2015/0313804 A1 | 11/2015 | Lynch et al. | |
| 2015/0313805 A1 | 11/2015 | Lynch et al. | |
| 2015/0313806 A1 | 11/2015 | Lynch et al. | |
| 2015/0313807 A1 | 11/2015 | Lynch et al. | |
| 2015/0313808 A1 | 11/2015 | Lynch et al. | |
| 2015/0313809 A1 | 11/2015 | Lynch et al. | |
| 2015/0313823 A1 | 11/2015 | Lockett et al. | |
| 2015/0315350 A1 | 11/2015 | Mao et al. | |
| 2016/0089314 A1* | 3/2016 | Marsh | A61K 8/0208 15/210.1 |
| 2016/0101026 A1 | 4/2016 | Pratt | |
| 2016/0101204 A1 | 4/2016 | Lynch | |
| 2016/0143825 A1 | 5/2016 | Pesaro et al. | |
| 2016/0143827 A1 | 5/2016 | Castan Barberan et al. | |
| 2016/0158134 A1 | 6/2016 | Disalvo | |
| 2016/0206533 A1* | 7/2016 | Callens | A61K 8/06 |
| 2016/0243007 A1 | 8/2016 | Constantine et al. | |
| 2016/0250109 A1 | 9/2016 | Dreher et al. | |
| 2016/0361242 A1 | 12/2016 | Durtschi et al. | |
| 2016/0367104 A1 | 12/2016 | Dreher et al. | |
| 2017/0056300 A1 | 3/2017 | Constantine et al. | |
| 2017/0056301 A1 | 3/2017 | Constantine et al. | |
| 2017/0105917 A1 | 4/2017 | Iwata | |
| 2017/0121641 A1 | 5/2017 | Smith | |
| 2017/0202760 A1* | 7/2017 | Callens | A61K 8/416 |
| 2017/0335080 A1 | 11/2017 | Mao et al. | |
| 2018/0028435 A1 | 2/2018 | Punsch et al. | |
| 2018/0071193 A1* | 3/2018 | Fields | C08L 5/08 |

(56) References Cited

U.S. PATENT DOCUMENTS

| | | | |
|---|---|---|---|
| 2018/0311135 | A1 | 11/2018 | Chang et al. |
| 2018/0311137 | A1* | 11/2018 | McKiernan .......... A61K 8/0208 |
| 2018/0333339 | A1 | 11/2018 | Hamersky |
| 2018/0333494 | A1 | 11/2018 | Lane et al. |
| 2018/0334644 | A1 | 11/2018 | Hamersky et al. |
| 2018/0360702 | A1 | 12/2018 | Demarcq et al. |
| 2019/0282457 | A1 | 9/2019 | Pratt |
| 2019/0282461 | A1 | 9/2019 | Glassmeyer |
| 2019/0350819 | A1 | 11/2019 | Hamersky et al. |
| 2020/0093710 | A1 | 3/2020 | Hamersky |
| 2020/0108003 | A1 | 4/2020 | Iwata et al. |
| 2020/0197272 | A1 | 6/2020 | Hertenstein et al. |
| 2020/0214946 | A1 | 7/2020 | Chan et al. |
| 2020/0308360 | A1 | 10/2020 | Mao et al. |
| 2020/0405587 | A1 | 12/2020 | Song |
| 2021/0000733 | A1 | 1/2021 | Hilvert |
| 2021/0094744 | A1 | 4/2021 | Benson et al. |
| 2021/0107263 | A1 | 4/2021 | Bartolucci et al. |
| 2021/0147763 | A1 | 5/2021 | Tan et al. |
| 2021/0161784 | A1 | 6/2021 | Zhao et al. |
| 2022/0168200 | A1 | 6/2022 | Zhao et al. |

FOREIGN PATENT DOCUMENTS

| | | | |
|---|---|---|---|
| CN | 1268558 | | 10/2000 |
| CN | 1357613 | A | 7/2002 |
| CN | 1530431 | A | 9/2004 |
| CN | 1583991 | A | 2/2005 |
| CN | 106726634 | A | 5/2017 |
| CN | 106728634 | A | 5/2017 |
| CN | 109589279 | B | 3/2020 |
| DE | 19607851 | A1 | 9/1997 |
| DE | 10331767 | A1 | 2/2005 |
| DE | 102010002863 | A1 | 9/2011 |
| DE | 102010026747 | A1 | 1/2012 |
| DE | DM100932 | | 4/2018 |
| DE | DM100938 | | 4/2018 |
| DE | DM101063 | | 5/2018 |
| DE | DM101100 | | 5/2018 |
| DE | DM101101 | | 5/2018 |
| EP | 609808 | A1 | 8/1994 |
| EP | 0858828 | A1 | 8/1998 |
| EP | 1206933 | A1 | 5/2002 |
| EP | 1217987 | B1 | 12/2004 |
| EP | 1160311 | B1 | 3/2006 |
| EP | 1808157 | A1 | 7/2007 |
| EP | 1958532 | A2 | 8/2008 |
| EP | 2085434 | A1 | 8/2009 |
| EP | 1317916 | B1 | 10/2010 |
| EP | 2606725 | A1 | 6/2013 |
| FR | 2871685 | A1 | 12/2005 |
| FR | 2886845 | A1 | 12/2006 |
| FR | 2992217 | A1 | 12/2013 |
| GB | 2235204 | A | 2/1991 |
| GB | 2355008 | A | 4/2001 |
| JP | 58021608 | | 2/1983 |
| JP | S58216109 | A | 12/1983 |
| JP | S6272609 | A | 4/1987 |
| JP | S6272610 | A | 4/1987 |
| JP | S6281432 | A | 4/1987 |
| JP | H01172319 | A | 7/1989 |
| JP | H01313418 | A | 12/1989 |
| JP | H0275650 | A | 3/1990 |
| JP | H05344873 | A | 12/1993 |
| JP | H0617083 | A | 1/1994 |
| JP | 0753349 | | 2/1995 |
| JP | H0789852 | A | 4/1995 |
| JP | H08325133 | A | 12/1996 |
| JP | H09216909 | A | 8/1997 |
| JP | H10251371 | A | 9/1998 |
| JP | H11322591 | A | 11/1999 |
| JP | 2000053998 | A | 2/2000 |
| JP | 2003073700 | A | 3/2003 |
| JP | 2003082397 | A | 3/2003 |
| JP | 2003113032 | A | 4/2003 |
| JP | 2004256799 | A | 9/2004 |
| JP | 2004345983 | A | 12/2004 |
| JP | 2005171063 | A | 6/2005 |
| JP | 2006097010 | A | 4/2006 |
| JP | 2007091954 | A | 4/2007 |
| JP | 2007197540 | A | 8/2007 |
| KR | 20020003442 | A | 1/2002 |
| KR | 20150049027 | A | 5/2015 |
| WO | 8301943 | A1 | 6/1983 |
| WO | 9514495 | A1 | 6/1995 |
| WO | 0112134 | A2 | 2/2001 |
| WO | 0119948 | A1 | 3/2001 |
| WO | 0125393 | A1 | 4/2001 |
| WO | 200125322 | A1 | 4/2001 |
| WO | 2001024770 | A1 | 4/2001 |
| WO | 2001054667 | A1 | 8/2001 |
| WO | 2004032859 | A1 | 4/2004 |
| WO | 2004041991 | A1 | 5/2004 |
| WO | 2005003423 | A1 | 1/2005 |
| WO | 2005070374 | A1 | 8/2005 |
| WO | 2005075547 | A1 | 8/2005 |
| WO | 2007033598 | A1 | 3/2007 |
| WO | 2007093558 | A1 | 8/2007 |
| WO | 2009016555 | A2 | 2/2009 |
| WO | 2009019571 | A1 | 2/2009 |
| WO | 2009095891 | A1 | 8/2009 |
| WO | 2010077627 | A2 | 7/2010 |
| WO | 2010085569 | A1 | 7/2010 |
| WO | 2011113501 | A1 | 9/2011 |
| WO | 2012120199 | A1 | 9/2012 |
| WO | 2012172207 | A2 | 12/2012 |
| WO | 2013150044 | A2 | 10/2013 |
| WO | 2014124070 | A1 | 8/2014 |
| WO | 2015053281 | A1 | 4/2015 |
| WO | 2018023180 | A1 | 2/2018 |
| WO | 2018098542 | A1 | 6/2018 |
| WO | 2019001940 | A1 | 1/2019 |
| WO | 2019014868 | A1 | 1/2019 |
| WO | 2019090098 | A1 | 5/2019 |
| WO | 2019142194 | A1 | 7/2019 |

OTHER PUBLICATIONS

Briscoe et al. "The effects of hydrogen bonding upon the viscosity of aqueous poly( vinyl alcohol) solutions," from Polymer, 41 (2000), pp. 3851-3860.

Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.

Hildebrand, T., et al. "Quantification of bone microarchitecture with the structure mode index", Computer Methods in Biomechanics and Biomedical Engineering, vol. 1, Jan. 14, 1997, pp. 15-23.

How Gemz work?, Gemz Hair Care, published on Oct. 1, 2018, retrieved on Apr. 27, 2021, retrieved from the Internet URL: https://www.youtube.com/watch?v=ts1waYk43g4.

https ://www.craftcuts.com/hexagon-craft-shape. htmlHexagon wood cutouts, www.craftcuts.com, 1 page, reviewed as early as May 2018 (Year: 2018).

Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.

Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/.

Unpublished U.S. Appl. No. 17/209,292, filed Mar. 23, 2021, to Jennifer Mary Marsh et. al.

Vaughan, C.D. "Solubility, Effects in Product, Package, Penetration and Preservation", Cosmetics and Toiletries, vol. 103, Oct. 1988.

Veslerby, A.: "Star Volume in Bone Research: A Histomorphometric Analysis Of Trabecular Bone Structure Using Vertical Sections", Anal Rec: Feb. 1993, 232(2), pp. 325-334.

Zhang et al. "Study on Morphology of Electrospun Poly( vinyl alcohol) Mats," European Polymer Journal 41 (2005), pp. 423-432.

All Office Actions; U.S. Appl. No. 17/398,024, filed Aug. 10, 2021.

(56) References Cited

OTHER PUBLICATIONS

All Office Actions; U.S. Appl. No. 17/398,025, filed Aug. 10, 2021.
All Office Actions; U.S. Appl. No. 17/398,020, filed Aug. 10, 2021.
Unpublished U.S. Appl. No. 17/398,020, filed Aug. 10, 2021, to Jean Jianqun Zhao et. al.
Unpublished U.S. Appl. No. 17/398,024, filed Aug. 10, 2021, to Jean Jianqun Zhao et. al.
Unpublished U.S. Appl. No. 17/398,025, filed Aug. 10, 2021, to Jean Jianqun Zhao et. al.
All Office Actions; U.S. Appl. No. 17/537,549, filed Nov. 30, 2021.

* cited by examiner

HAIR CONDITIONER COMPOSITIONS WITH A PRESERVATIVE SYSTEM CONTAINING SODIUM BENZOATE AND GLYCOLS AND/OR GLYCERYL ESTERS

FIELD OF THE INVENTION

The present invention relates to hair conditioner compositions, more particularly to hair conditioner compositions comprising a surfactant system that includes sodium benzoate and glycols and/or glyceryl esters.

BACKGROUND OF THE INVENTION

A variety of approaches have been developed to condition the hair. These approaches range from post-shampoo application of hair conditioners such as leave-on and rinse-off products, to hair conditioning shampoos which attempt to both clean and condition the hair from a single product.

Although some consumers prefer the ease and convenience of a shampoo which includes conditioners, a substantial proportion of consumers prefer the more conventional conditioner formulations which are applied to the hair as a separate step from shampooing, usually subsequent to shampooing. Conditioning formulations can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or amount of hair.

It is known that conditioning compositions, like most cosmetic products, contain preservatives to prevent product spoilage by microorganisms. Preservatives can help keep the product stable throughout the life of the product including during shipping, handling, storage, and while the consumer is using the product. During use, the consumer can inadvertently introduce microorganisms as they open and close the aqueous product and these microorganisms can proliferate in the warm, humid environment of the shower. Therefore, cosmetic products generally contain preservation systems. Common preservatives in conditioner products can include isothiazolinones, parabens, benzyl alcohol, phenoxyethanol, and ethylenediaminetetraacetic acid (EDTA) and salts thereof.

However, some consumers want cosmetic products with preservation systems that are EWG VERIFIED™, do not contain any of the ingredients that Whole Foods® lists as unacceptable, and is categorized as "risk-free" (green dot) by the Yuka® Application. Modifying the preservation system to reduce or eliminate certain preservatives can have a negative impact on microbiological safety requirements.

Therefore, there is a need for a conditioner composition with an effective preservation system that that is EWG VERIFIED™, does not contain any of the ingredients that Whole Foods® Market lists as unacceptable, and is categorized as "risk-free" by the Yuka® Application.

SUMMARY OF THE INVENTION

A hair conditioner composition comprising: (a) from about 50% to about 95% of an aqueous carrier, by weight of the composition; (b) from about 0.1 wt % to about 10 wt % of a cationic surfactant; (c) from about 1.5 wt % to about 15 wt % of a high melting point fatty compound; (d) a preservation system comprising: (i) from about 0.1% to about 0.5% sodium benzoate, by weight of the composition; (ii) from about 0.3% to about 1.5% of a second composition selected from the group consisting of glycol, glyceryl ester, and combinations thereof; wherein the ratio of sodium benzoate to the second composition is from about 1:4 to about 1:1; wherein the conditioner composition comprises a gel network.

A hair conditioner composition comprising: (a) from about 50% to about 95% of an aqueous carrier, by weight of the composition; (b) from about 0.1 wt % to about 10 wt % of a cationic surfactant selected from the group consisting of wherein the cationic surfactant is selected from the group consisting of behenamidopropyl dimethylamine (BAP-DMA), behentrimonium chloride, cetrimonium chloride, stearamidopropyl dimethylamine, and combinations thereof; (c) from about 1.5 wt % to about 15 wt % of a fatty alcohol selected from the group consisting of cetyl alcohol, stearyl alcohol, behenyl alcohol, brassica alcohol; (d) a preservation system comprising: (i) from about 0.1% to less than 0.4% sodium benzoate, by weight of the composition; (ii) from about 0.3% to about 1.5% of a glycol selected from the group consisting of glycols can include butylene glycol, pentylene glycol, hexylene glycol, 1,2-hexanediol, caprylyl glycol, decylene glycol, and mixtures thereof; wherein the ratio of sodium benzoate to the glycol is less than 1:1; wherein the conditioner composition comprises a gel network.

A hair conditioner composition comprising: (a) from about 50% to about 95% of an aqueous carrier, by weight of the composition; (b) from about 0.1 wt % to about 10 wt % of a cationic surfactant selected from the group consisting of wherein the cationic surfactant is selected from the group consisting of behenamidopropyl dimethylamine (BAP-DMA), behentrimonium chloride, cetrimonium chloride, stearamidopropyl dimethylamine, and combinations thereof; (c) from about 1.5 wt % to about 15 wt % of a fatty alcohol selected from the group consisting of cetyl alcohol, stearyl alcohol, behenyl alcohol, brassica alcohol; (d) a preservation system comprising: (i) from about 0.1% to less than 0.4% sodium benzoate, by weight of the composition; (ii) from about 0.3% to about 1.5% of a glycol selected from the group consisting of glycols can include butylene glycol, pentylene glycol, hexylene glycol, 1,2-hexanediol, caprylyl glycol, decylene glycol, and mixtures thereof; wherein the ratio of sodium benzoate to the glycol is less than 1:1; wherein the conditioner composition comprises a gel network.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

While the specification concludes with claims particularly pointing out and distinctly claiming the invention, it is believed that the present invention will be better understood from the following description.

Hair conditioners are used to improve the feel, appearance, and manageability of the hair. Hair conditioning compositions generally include a cationic surfactant, high melting point fatty compound(s) having a melting point of greater than 25° C. and in some examples from 40 to 85° C., and an aqueous carrier. Conditioning compositions also include a safe and effective preservation system to prevent the growth of microbes under regular storage and usage conditions. Common preservatives in conditioner products can include isothiazolinones (including methylisothiazolinone and a mixture of methylisothiazolinone and methylchloroisothiazolinone (commercially available as Kathon™ from Dow®), parabens (including Germaben®, methylparben, propylparaben, butylparaben, and phenoxyethanols, which are commercially available in Optiphen™ and Optiphen™ Plus from Ashland™), benzyl alcohol, and phenoxyethanol. Ethylenediaminetetraacetic acid (EDTA) and salts thereof including disodium EDTA, calcium disodium EDTA, and tetrasodium EDTA, are also frequently used in hair care compositions as a chelator that can also improve product performance and stability.

However, there is growing demand from some consumers for a conditioner product and/or a preservation system that meets at least one, two, or all three of the following standards:
  EWG VERIFIED™ (according to the criteria, as of Nov. 25, 2019), which includes meeting the Environmental Working Group's (EWG) criteria including avoiding EWG's ingredients of concern, having fully transparent labeling, and using good manufacturing practices, in addition to other criteria described in EWG's Licensing Criteria: Personal Care Products (2019).
  Does not contain any of ingredients that Whole Foods® lists as unacceptable lists as unacceptable in its Premium Body Care Unacceptable Ingredients (July 2018)
  Categorized as "risk-free" (green dot) by the Yuka® Application (March 2019)

However, replacing traditional preservatives with preservatives that meet the standards, listed above, while maintaining antimicrobial effectiveness and product performance can be challenging. Table 1 and Table 2, below, include examples that have a sodium benzoate preservative, which meets the standards. However, if the conditioner composition had a smooth and creamy consistency, then the level of sodium benzoate was too low to effectively inhibit the growth of microbes. When the level of sodium benzoate was increased, the conditioner composition was too thin to easily apply with a user's hands, which can significantly impact product performance and the usage experience. As shown in Table 3 and described in accompanying text, a preservation system with sodium benzoate and a glycol, such as caprylyl glycol, or glyceryl esters, such as glyceryl caprylate/caprate and glyceryl caprylate (and) glyceryl undecylenate can be effective if the proper levels of each ingredient are added. It was found that a preservation system that contains sodium benzoate and a second composition selected from the group consisting of glycols, glyceryl esters, and combinations thereof contains all of the ingredients that have a EWG rating score of equal to or less than 3, can be EWG VERIFIED™, may not contain any of the ingredients that Whole Foods® Market lists as unacceptable, and can categorized as "risk-free" by the Yuka® Application, can maintain antimicrobial effectiveness, and can provide good conditioning performance. In some examples, the preservation system and/or the conditioner can also meet the COS-MOS-standard (Jan. 1, 2019). The conditioner compositions containing this preservation system can have a uniform, smooth, creamy appearance and have an effective preservation system where the level of microbes (both bacteria and fungi) is undetectable (>99.99% reduction) as determined by the Bacterial and Fungal Microbial Susceptibility Test Methods, as described herein.

The second composition can contain a glycol and/or a glyceryl ester. Glycols and glyceryl esters both have two —OH groups on the molecule. Non-limiting examples of glycols can include butylene glycol, pentylene glycol, hexylene glycol, 1,2-hexanediol, caprylyl glycol, decylene glycol (1,2-decanedioi) and mixtures thereof. In one example, the glycol can be carpylyl Non-limiting examples of glycerol esters can include glyceryl caprylate, glyceryl caprate, glyceryl undecylenate and mixtures thereof.

The conditioner composition and/or preservation system can be free of or substantially free of certain preservatives, in particular preservatives that do not meet one or more of the standards, such as isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, and/or parabens. The conditioner composition can be free of or substantially free of ethylenediaminetetraacetic acid (EDTA) and salts thereof. In addition to meeting the standards for a cationic surfactant and preservation system, some consumers prefer a conditioner composition that is free of or substantially free of the following: silicone, propellants, phthalates, parabens, isothiazolinones (e.g. Kathon™), phenoxyethanols, dyes, sulfates, and/or formaldehyde donors. The conditioner composition can also be vegan.

The conditioner composition can contain from about 0.2 wt % to about 1.5 wt % preservation system, alternatively from about 0.3 wt % to about 1.25 wt % preservation system, alternatively from about 0.4 wt % to about 1 wt % preservation system, alternatively from 0.5 wt % to about 0.8 wt % preservation system, and alternatively from about 0.6 wt % to about 0.8 wt % preservation system.

The conditioner composition can contain from about 0.05 wt % to about 0.8 wt % sodium benzoate, alternatively 0.1 wt % to about 0.5 wt % sodium benzoate, alternatively from about 0.2 wt % to about 0.4 wt % sodium benzoate. The conditioner composition can contain sodium benzoate and can contain less than 2% sodium benzoate, alternatively less than 1.5% sodium benzoate, alternatively less than 1% sodium benzoate, alternatively less than 0.8% sodium benzoate, alternatively less than 0.6 wt % sodium benzoate, and alternatively less than 0.5% sodium benzoate.

The preservation system can contain from about 20% to about 50% sodium benzoate, by weight of the preservation system, alternatively from about 25% to about 50% sodium benzoate, by weight of the preservation system, from about 30% to about 50% sodium benzoate, by weight of the preservation system, and from about 30% to about 40% sodium benzoate, by weight of the preservation system.

The conditioner composition can contain from about 0.3 wt % to about 1.5 wt % of a second composition, alternatively from about 0.32 wt % to about 1 wt %, alternatively from about 0.33 wt % to about 0.8 wt %, alternatively from about 0.34 wt % to about 0.6 wt %, alternatively from about 0.35 wt % to about 0.5 wt %, alternatively from about 0.37 wt % to about 0.45 wt %, and alternatively from about 0.38 wt % to about 0.43 wt %. If the conditioner composition contains too much glycol and/or glyceryl ester the gel network structure may be destroyed, and the conditioner will not have consumer acceptable rheology and/or performance.

The preservation system can contain from about 50% to about 80% of the second composition, by weight of the preservation system, alternatively from about 50% to about 75%, by weight of the preservation system, alternatively from about 50% to about 70%, by weight of the preservation system, and alternatively from about 50% to about 67%, by weight of the preservation system.

The weight ratio of sodium benzoate to the second composition can be from about 1:4 to about 1:1, alternatively from about 1:3 to about 1:1, alternatively from about 1:2 to about 1:1, and from about 1:1.7 to about 1:1.

The conditioner composition can have a shear stress from about 50 Pa to about 500 Pa, alternatively from about 75 Pa to about 450 Pa, from about 100 Pa to about 400 Pa, from about 125 Pa to about 375 Pa, from about 130 Pa, to about 350 Pa, and from about 135 Pa to about 325 Pa. The shear stress can be determined using the Shear Stress Test Method, described hereafter.

The conditioner composition can have a pH of less than 5. Alternatively, the conditioner composition can have a pH from about 2.5 to about 5, alternatively from about 3.5 to about 4.5. The pH can be determined using the pH Test Method, described hereafter.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, the terms "include," "includes," and "including," are meant to be non-limiting and are understood to mean "comprise," "comprises," and "comprising," respectively.

As used herein, the term "free of" means that 0% of an ingredient was intentionally added to the conditioner composition, or the conditioner composition comprises 0% of an ingredient by total weight of the composition, thus no detectable amount of the stated ingredient.

The term "substantially free of" as used herein means less than 0.5%, less than 0.3%, less than 0.1%, less than 0.05%, less than 0.01%, or less than an immaterial amount of a stated ingredient by total weight of the composition.

As used herein, "mixtures" is meant to include a simple combination of materials and any compounds that may result from their combination.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Cationic Surfactant

The compositions of the present invention can comprise a cationic surfactant. The cationic surfactant can be included in the composition at a level of from about 0.1%, alternatively from about 0.5%, alternatively from about 0.8%, alternatively from about 1.0%, and to about 20%, alternatively to about 10%, alternatively to about 8.0%, alternatively to about 6.0% by weight of the composition, in view of providing the benefits of the present invention.

The surfactant can be water-insoluble. In the present invention, "water-insoluble surfactants" means that the surfactants have a solubility in water at 25° C. of alternatively below 0.5 g/100 g (excluding 0.5 g/100 g) water, alternatively 0.3 g/100 g water or less.

Cationic surfactant can be one cationic surfactant or a mixture of two or more cationic surfactants. Alternatively, the cationic surfactant is selected from: a mono-long alkyl amine; a di-long alkyl quaternized ammonium salt; a mono-long alkyl cationic neutralized amino acid esters; a combination of a mono-long alkyl amine and a di-long alkyl quaternized ammonium salt; and a combination of a mono-long alkyl amine and a mono-long alkyl cationic neutralized amino acid esters.

In some examples, the conditioner composition can be substantially free of or free of cationic surfactants that have a quaternized ammonium salt.

Mono-Long Alkyl Amine

Mono-long alkyl amine can include those having one long alkyl chain of alternatively from 19 to 30 carbon atoms, alternatively from 19 to 24 carbon atoms, alternatively from 20 to 24 carbon atoms, alternatively from 20 to 22 alkyl group. Mono-long alkyl amines can include mono-long alkyl amidoamines Primary, secondary, and tertiary fatty amines can be used.

Tertiary amido amines having an alkyl group of from about 19 to about 22 carbons. Exemplary tertiary amido amines include: behenamidopropyldimethylamine, behenamidopropyldiethylamine, behenamidoethyldiethylamine, behenamidoethyldimethylamine, brassicamidopropyldimethylamine, brassicamidopropyldiethylamine, brassicamidoethyldiethylamine, brassicamidoethyldimethylamine Amines in the present invention are disclosed in U.S. Pat. No. 4,275,055, Nachtigal, et al.

In some examples, the conditioner composition can be substantially free of or free of stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethylamine, palmitamidoethyldimethylamine, arachidamidopropyldimethylamine, arachidamidopropyldiethyl amine, arachidamidoethyldiethylamine, arachidamidoethyldimethylamine, and/or diethylaminoethylstearamide.

These amines are used in combination with acids such as 1-glutamic acid, lactic acid, hydrochloric acid, malic acid, succinic acid, acetic acid, fumaric acid, tartaric acid, citric acid, 1-glutamic hydrochloride, maleic acid, and mixtures thereof; alternatively 1-glutamic acid, lactic acid, citric acid, at a molar ratio of the amine to the acid of from about 1:0.3 to about 1:2, alternatively from about 1:0.4 to about 1:1.

In some examples, the conditioner composition can be free of mono long alkyl quaternized ammonium salts.

Di-Long Alkyl Quaternized Ammonium Salts

When used, di-long alkyl quaternized ammonium salts are alternatively combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts can have two long alkyl chains of from 12 to 30 carbon atoms, alternatively from 16 to 24 carbon atoms, alternatively from 18 to 22 carbon atoms. Such di-long alkyl quaternized ammonium salts can have the formula (I):

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Alternatively, two of $R^{71}$, $R^{72}$, $R^{73}$ and $R^{74}$ are selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Di-long alkyl cationic surfactants can include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 1.0%, alternatively from about 1.5%, alternatively from about 2.0%, alternatively from about 2.5%, even alternatively from about 3%, and to about 30%, alternatively to about 15%, alternatively to about 8.0%, alternatively to about 7% by weight of the composition, in view of providing the benefits of the present invention.

The high melting point fatty compound can have a melting point of 25° C. or higher, alternatively 40° C. or higher, alternatively 45° C. or higher, alternatively 47° C. or higher, alternatively 49° C. or higher, in view of stability of the emulsion especially the gel network. Alternatively, such melting point is up to about 90° C., alternatively up to about 80° C., alternatively up to about 75° C., even alternatively up to about 71° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound can be selected from the group consisting of fatty alcohols, fatty acids, and mixtures thereof. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are alternatively used in the composition of the present invention. The fatty alcohols can have from about 14 to about 30 carbon atoms, alternatively from about 16 to about 22 carbon atoms. These fatty alcohols are saturated and can be straight or branched chain alcohols.

Fatty alcohols can include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl, brassica or behenyl group.

The fatty alcohol can be a mixture of cetyl alcohol and stearyl alcohol.

Generally, in the mixture, the weight ratio of cetyl alcohol to stearyl alcohol is alternatively from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of alternatively from about 1:1 to about 4:1, alternatively from about 1:1 to about 2:1, alternatively from about 1.2:1 to about 2:1, in view of avoiding to get too thick for spreadability. It may also provide more conditioning on damaged part of the hair.

Aqueous Carrier

The composition of the present invention can include an aqueous carrier. The level and species of the carrier can be selected according to the compatibility with other components, and other desired characteristic of the product.

The carrier can include water and water solutions of lower alkyl alcohols. The lower alkyl alcohols can be monohydric alcohols having 1 to 6 carbons, alternatively ethanol and isopropanol.

Alternatively, the aqueous carrier is substantially water. Deionized water is alternatively used. Water from natural sources including mineral cations can also be used, depending on the desired characteristic of the product. Generally, the compositions of the present invention comprise from about 40% to about 99%, alternatively from about 50% to about 95%, and alternatively from about 70% to about 93%, and alternatively from about 80% to about 92% water.

Gel Network

The gel network composition can be included in conditioner compositions to provide conditioning benefits, including improved wet feel of the hair after rinsing the conditioner. As used herein, the term "gel network" refers to a lamellar or vesicular solid crystalline phase which comprises at least one high melting point fatty compound, such as a fatty alcohol, as specified below, at least one surfactant, in particular a cationic surfactant, as specified below, and water or other suitable solvents. The lamellar or vesicular phase comprises bi-layers made up of a first layer comprising the high melting point fatty compound and the surfactant and alternating with a second layer comprising the water or other suitable solvent. Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International*, Vol. 7, 63-70 (1986).

A gel network can be formed by the cationic surfactant, the high melting point fatty compound, and an aqueous carrier. The gel network is suitable for providing various conditioning benefits, such as slippery feel during the application to wet hair and softness and moisturized feel on dry hair.

Alternatively, when the gel network is formed, the cationic surfactant and the high melting point fatty compound are contained at a level such that the weight ratio of the cationic surfactant to the high melting point fatty compound is in the range of, alternatively from about 1:1 to about 1:10, alternatively from about 1:1.5 to about 1:7, alternatively from about 1:2 to about 1:6, in view of providing improved wet conditioning benefits.

Alternatively, especially when the gel network is formed, the composition of the present invention is substantially free of anionic surfactants, in view of stability of the gel network. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, alternatively 1% or less, alternatively 0.5% or less, alternatively 0.1% or less by weight of the composition. Most alternatively, the total level of such anionic surfactants is 0% by weight of the composition.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, alternatively up to about 5% by weight of the composition.

A wide variety of other additional components can be formulated into the present compositions. These include: other conditioning agents such as aloe vera gel; aloe barbadensis leaf juice; *Ecklonia radiata* extract; natural oils and waxes with shea butter, safflower oil, cocoa butter, orange peel wax, olive oil, macadamia seed oil, *Oenothera biennis* oil, *Crambe abyssinica* see oil, argon oil, camelina oil, sunflower oil, almond oil, argania spinosa kernel oil, grape see oil, jojoba oil, coconut oil, meadowfoam seed oil, neem oil, linseed oil, castor oil, soybean oil, sesame oil, beeswax, sunflower wax, candelilla wax, rice bran wax, carnauba wax, bayberry wax and soy wax; essential oils such as lime peel oil, lavender oil, peppermint oil, cedarwood oil, tea tree oil, ylang-ylang oil and coensage oil which can be used in fragrance; hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate; antioxidants include: rosemary, tocopherol, vitamin E, vitamin A, tea extracts, and hydroxyacetophenone (available as Symsave® H from Symrise®); amino acids include histidine, 1-arginine and others.

Test Methods

Bacterial Microbial Susceptibility Testing Method

Bacterial microbial susceptibility testing is used to assess the anti-bacterial effectiveness of the preservation system in cosmetic rinse-off conditioner.

A bacterial pool (mixture in equal volumes) of challenge organisms used in the test is comprised of standardized solutions of the bacterial strains *Escherichia coli* (ATCC#8739), *Staphylococcus aureus* (ATCC#6538), *Pseudomonas aeruginosa* (ATCC#9027), *Burkholderia cepacia* (ATCC#25416), as well as *Klebsiella pneumoniae, Enterobacter* gergoviae and *Serratia marcescens* strains isolated from cosmetic products. The bacterial pool is prepared to have a concentration of approximately 6-8 log cfu/ml. To start the test, 0.1 ml of the bacterial pool is added into 10.0 g of a test conditioner. The test conditioner is then incubated for 2 days at 20-25° C. After incubation, a 1.0 g aliquot of product is neutralized using Modified Letheen Broth containing 1.5% polysorbate 80 (commercially available as Tween® 80 from Croda™) and 1% Lecithin to aid in microbial recovery/enumeration. Then, multiple diluted concentrations of this sample are transferred into petri dishes containing Modified Letheen Agar with 1.5% Tween® 80, and the agar plates are incubated at least 2 days at 30-35° C. Bacterial colony forming units (cfus) are then enumerated, and a bacterial log reduction from the starting log cfu/g challenge level is reported.

A 1 log cfu/g reduction equates to ~a 90% bacterial reduction. A 2 log cfu/g reduction equates to ~a 99% bacterial reduction. A 3 log cfu/g reduction equates to ~a 99.9% bacterial reduction. A 4 log cfu/g reduction equates to ~a 99.99% bacterial reduction. Greater log cfu/g reduction values indicate greater antimicrobial robustness from the preservation system.

Fungal Microbial Susceptibility Testing Method:

Fungal microbial susceptibility testing is used to assess the anti-fungal effectiveness of the preservation system in cosmetic rinse-off conditioner.

Standardized ATCC strains of the yeast *Candida albicans* (ATCC#10231) and mold *Aspergillus brasiliensis* (frm. *niger*) (ATCC#16404) are mixed in 1:1 (v:v) ratio, and this fungal pool is used as inoculum in the test. The concentration of the fungal pool is approximately 6-8 log cfu/ml. To start the test, 0.1 ml of the fungal pool is added into 10.0 g of a testing conditioner. After the inoculated sample is incubated for 2 days at 20-25° C., a 1.0 g aliquot of product is neutralized using Modified Letheen Broth containing 1.5% Tween® 80 and 1% Lecithin to aid in microbial recovery/enumeration. Then, multiple diluted concentrations of this sample are transferred into petri dishes containing Modified Letheen Agar with 1.5% Tween 80, and the agar plates are incubated for at least 5 days at 20-25° C., at which time fungal colony forming units (cfus) are then enumerated, and a fungal log reduction from the starting log cfu/g challenge level is calculated.

A 1 log cfu/g reduction equates to ~a 90% fungal reduction. A 2 log cfu/g reduction equates to ~a 99% fungal reduction. A 3 log cfu/g reduction equates to ~a 99.9% fungal reduction. A 4 log cfu/g reduction equates to ~a 99.99% fungal reduction. Greater log cfu/g reduction values indicate greater anti-fungal robustness from the preservation system.

Shear Stress

Shear stress is measured by shear rate sweep condition with a rheometer available from TA Instruments with a mode name of ARG2. Geometry has 40 mm diameter, 2° C. cone angle, and gap of 49 µm. Shear rate is logarithmically increased from 0 to 1200/s for 1 min, and temperature is kept at 26.7° C. Share stress at a high shear rate of 950/s is measured and defined above.

pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimiwipe®. Submerse the electrode in the pH 4 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe.

Submerse the electrode into the testing sample and press the read button. Wait until the pH icon stops flashing and record the value.

EXAMPLES

The following are non-limiting examples of the conditioner compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

The examples in Tables 1-3 were made as follows. Sodium benzoate and L-glutamic were dissolved in the water. The mixture was heated to 80° C. Then, the cationic surfactant and fatty alcohols were added to the mixture. Next, the mixture was cooled while the cationic surfactant and fatty alcohols continue to dissolve. Then, glycols or glyceryl esters were added, followed by oils and perfume when the temperature was below 45° C. The composition was cooled to room temperature to make the conditioner composition.

In Tables 1-3, below, the Micro~Bacteria @ 2 days and the Micro-Fungi @ 2 days is determined by the Bacterial and Fungal Microbial Susceptibility Test Methods, described herein. In order for the preservation system to be effective, the level of microbes (bacteria and fungi) needs to be undetectable, which means that there is a greater than 99.99% reduction in microbes at two days as determined by the Bacterial and Fungal Microbial Susceptibility Test Methods. In Table 2, below, N/A indicates that the test was not performed.

TABLE 1

| Comp. Examples 1-6 | | | | | | |
|---|---|---|---|---|---|---|
| | Comp. Ex. 1 | Comp. Ex. 2 | Comp. Ex. 3 | Comp. Ex. 4 | Comp. Ex. 5 | Comp. Ex. 6 |
| Appearance | Creamy and smooth | | | | | |
| Sheer stress (Pa) @950 1/s | 350 | 419 | 448 | 450 | 354 | 343 |
| Micro - Bacteria @ 2 days | ~90% reduction | Not Detectable (>99.99% reduction) | | | | |
| Micro - Fungi @ 2 days | ~90% reduction | | | >99% reduction | | |
| Sodium Benzoate wt % (active) [1] | — | 0.20 | 0.25 | 0.40 | 0.20 | 0.25 |
| Caprylyl Glycol wt % (active) [2] | — | — | — | — | 0.20 | 0.20 |
| Behenamidopropyl Dimethylamine (Cationic Surfactant) wt % (active) [6] | 3.74 | 3.74 | 3.74 | 3.74 | 3.74 | 3.74 |
| L-Glutamic Acid wt % (active) [7] | 1.55 | 1.55 | 1.55 | 1.55 | 1.55 | 1.55 |
| Cetyl Alcohol (C16 Fatty alcohol) wt % (active) [8] | 3.83 | 3.83 | 3.83 | 3.83 | 3.83 | 3.83 |
| Stearyl Alcohol (C18 Fatty Alcohol) wt % (active) [9] | 2.84 | 2.84 | 2.84 | 2.84 | 2.84 | 2.84 |

TABLE 1-continued

| | Comp. Examples 1-6 | | | | | |
|---|---|---|---|---|---|---|
| | Comp. Ex. 1 | Comp. Ex. 2 | Comp. Ex. 3 | Comp. Ex. 4 | Comp. Ex. 5 | Comp. Ex. 6 |
| Citric Acid wt % | 0.25 | 0.25 | 0.35 | 0.25 | 0.25 | 0.35 |
| Distilled Water | Q.S. | Q.S. | Q.S. | Q.S. | Q.S. | Q.S. |
| pH | 3.9 | 4.2 | 4.2 | 4.3 | 4.2 | 4.2 |

TABLE 2

| | Comparative Examples 7-11 | | | | |
|---|---|---|---|---|---|
| | Comp. Ex. 7 | Comp. Ex. 8 | Comp. Ex. 9 | Comp. Ex. 10 | Comp. Ex. 11 |
| Appearance | Creamy and smooth | | | Clumpy and grainy | Thin and grainy |
| Sheer stress (Pa) @950 1/s | 270 | 275 | 271 | N/A | |
| Micro - Bacteria @ 2 day | Not Detectable (>99.99% reduction) | | | N/A | |
| Micro - Fungi @ 2 days | >90% reduction | >99% reduction | | N/A | |
| Sodium Benzoate wt % (active)[1] | 0.20 | 0.20 | 0.20 | 1.00 | — |
| Caprylyl Glycol wt % (active)[2] | — | — | — | — | 2.00 |
| Glyceryl Caprylate/Caprate wt % (active)[3] | 0.40 | — | — | — | — |
| Glyceryl Caprylate (and) Glyceryl Undecylenate wt % (active)[4] | — | 0.40 | — | — | — |
| Behentrimonium Chloride (Cationic Surfactant) wt % (active)[5] | — | — | 2.28 | — | — |
| Behenamidopropyl Dimethylamine (cationic surfactant) wt % (active)[6] | 3.74 | 3.74 | — | 3.74 | 3.74 |
| L-Glutamic Acid wt % (active)[7] | 1.55 | 1.55 | — | 1.55 | 1.55 |
| Cetyl Alcohol (C16 Fatty alcohol) wt % (active)[8] | 3.83 | 3.83 | 1.67 | 3.83 | 3.83 |
| Stearyl Alcohol (C18 Fatty Alcohol) wt % (active)[9] | 2.84 | 2.84 | 4.50 | 2.84 | 2.84 |
| Citric Acid | 0.25 | 0.25 | 0.035 | 1.25 | 0.25 |
| Distilled Water | Q.S. | Q.S. | Q.S. | Q.S. | Q.S. |
| pH | 4 | 4.1 | 4.4 | 4 | 4.1 |

Comparative Example 1 is the control and does not contain a preservation system. Comparative Example 1 does not provide enough microbe reduction at 2 days for bacteria and fungi.

Comparative Examples 2, 3, and 4 contain 0.20 wt %, 0.25 wt %, and 0.40 wt % sodium benzoate and these examples have an undetectable level (>99.99% reduction) of bacteria at two days. However, a preservation system that contains only sodium benzoate at these levels does not provide enough fungi reduction at two days, as these examples only have a ~90% reduction.

Comparative Examples 5 and 6 include a preservation system that has both sodium benzoate and caprylyl glycol. These examples have an undetectable level (>99.99% reduction) of bacteria at two days. The combination of sodium benzoate and caprylyl glycol improves the reduction of fungi at 2 days, as compared to Comparative Examples 2, 3, and 4. However, there is still a detectable level of fungi and therefore the preservation system in these examples is not considered effective.

Comparative Example 7 has a preservation system with 0.20 wt % sodium benzoate and 0.40 wt % glyceryl caprylate/caprate (a glyceryl ester) and this example has an undetectable level (>99.99% reduction) of bacteria at two days. However, it has a >90% reduction in fungi at two days and is ineffective.

Similar to Comparative Example 7, Comparative Example 8 has a preservation system with 0.20 wt % sodium benzoate and 0.40 wt % glyceryl caprylate (and) glyceryl undeylenate and this example has an undetectable level (>99.99% reduction) of bacteria at two days. However, it has a >90% reduction in fungi at two days and is ineffective.

Comparative Example 9 contains 0.20% sodium benzoate and behentrimonium chloride (cationic surfactant) and this example has an undetectable level (>99.99% reduction) of bacteria at two days. However, it has a detectable level of fungi (>99% reduction) at two days and is therefore ineffective.

Figure 1:
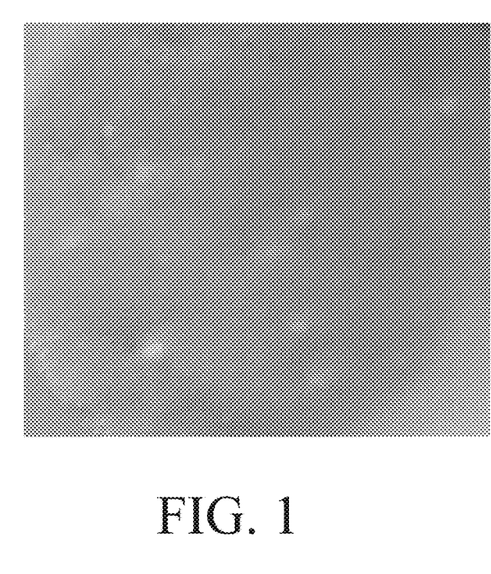
FIG. 1 is a photograph of the conditioner composition of Comparative Example 10, which contains 1 wt % sodium benzoate and has a clumpy and grainy appearance.

Comparative Example 10 contains 1 wt % sodium benzoate. As shown in FIG. 1, instead of being a smooth, creamy conditioner, it was clumpy and grainy, which is not consumer preferred. While not willing to be bound by theory, it is believed that the sodium benzoate level in this example is too high and since sodium benzoate is a salt, it effects the packing of the gel network. For example, in this example it is believed that some regions the gel network may be packed too tight and this can lead to the clumpy texture.

Figure 2:
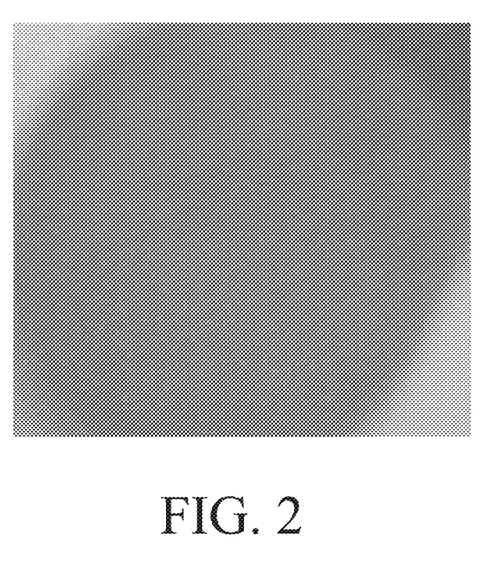
FIG. 2 is a photograph of the conditioner composition of Comparative Example 11, which contains 2 wt % sodium benzoate and has a thin and grainy appearance.

Comparative Example 11 contains 2 wt % caprylyl glycol. As shown in FIG. 2, instead of being a smooth, creamy conditioner, it was thin and crystalline appearance. A conditioner with this texture could be difficult for a consumer to apply with their hands and may not provide good conditioning. While not willing to e bound by theory, it is believed that if the level of glycol is too high, it acts like a solvent and breaks down the gel network.

TABLE 3

Examples 1-5

| | Ex. 1 | Ex. 2 | Ex. 3 | Ex. 4 | Ex. 5 |
|---|---|---|---|---|---|
| Appearance | Creamy and smooth | | | | |
| Sheer stress (Pa) @950 1/s | 304 | 302 | 289 | 290 | 141 |
| Micro - Bacteria @ 2 days | Not Detectable (>99.99% reduction) | | | | |
| Micro - Fungi @ 2 days | Not Detectable (>99.99% reduction) | | | | |
| Sodium Benzoate wt % (active)[1] | 0.20 | 0.25 | 0.40 | 0.40 | 0.20 |
| Caprylyl Glycol wt % (active)[2] | 0.40 | 0.40 | — | — | 0.40 |
| Glyceryl Caprylate/Caprate wt % (active)[3] | — | — | 0.40 | — | — |
| Glyceryl Caprylate (and) Glyceryl Undecylenate wt % (active)[4] | — | — | — | 0.40 | — |
| Behentrimonium Chloride (Cationic Surfactant) wt % (active)[5] | — | — | — | — | 2.28 |
| Behenamidopropyl Dimethylamine (Cationic Surfactant) wt % (active)[6] | 3.74 | 3.74 | 3.74 | 3.74 | — |
| L-Glutamic Acid wt % (active)[7] | 1.55 | 1.55 | 1.55 | 1.55 | — |
| Cetyl Alcohol (C16 Fatty alcohol) wt % (active)[8] | 3.83 | 3.83 | 3.83 | 3.83 | 1.67 |
| Stearyl Alcohol (C18 Fatty Alcohol) wt % (active)[9] | 2.84 | 2.84 | 2.84 | 2.84 | 4.50 |
| Citric Acid | 0.25 | 0.35 | 0.25 | 0.25 | 0.035 |
| Distilled Water | Q.S. | Q.S. | Q.S. | Q.S. | Q.S. |
| pH | 4.2 | 4.2 | 4.1 | 4.1 | 4.4 |

[1]Sodium Benzoate, available from Kalama ®
[2]Caprylyl Glycol, available from Procter and Gamble ®
[3]Glyceryl Caprylate/Caprate (STEPAN-MILD ® GCC), available from Stepan ®
[4]Glyceryl Caprylate (and) Glyceryl Undecylenate (Lexgard ® Natural), available from Index ®
[5]Behentrimonium Chloride/IPA (Genamin KDMP), available from Clariant ™ at 80% active level
[6]Behenamidopropyl Dimethylamine (BAPDMA) (Incromine ™ BD), available from Croda ®
[7]L-Glutamic Acid, available from Ajinomoto ®
[8]Cetyl alcohol, 95% active level available from Procter & Gamble ®
[9]Stearyl alcohol, 97% active level, available from Procter & Gamble ®

Figure 3:
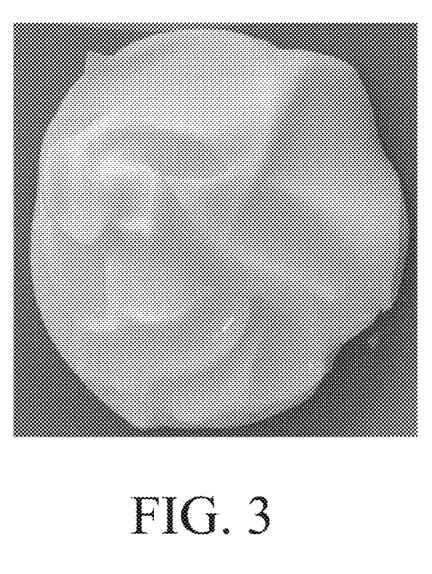
FIG. 3 is a photograph of the conditioner composition of Example 1, which contains 0.20 wt % sodium benzoate and 0.40 wt % caprylyl glycol.

All of the Examples in Table 3 have preservation systems that are effective (i.e. bacteria and fungi are not detectable (>99.99% reduction) at 2 days) and a creamy and smooth appearance that is consumer preferred. FIG. 3 is a photograph of Example 1 that shows the smooth and creamy appearance of the conditioner composition. These examples have between 0.20-0.40 wt % sodium benzoate and 0.40 wt % caprylyl glycol, glyceryl caprylate/caprate, or glyceryl caprylate (and) glyceryl undecylenate. The weight ratio of sodium benzoate to caprylyl glycol, glyceryl caprylate/caprate, or glyceryl caprylate (and) glyceryl undecylenate is from about 1:2 to about 1:1.

All of the Examples in Table 3 have a creamy and smooth appearance that can be consumer preferred.

Combinations:
A. A hair conditioner composition comprising:
  a. an aqueous carrier;
  b. a cationic surfactant;
  c. a high melting point fatty compound;
  d. a preservation system comprising:
    i. sodium benzoate;
    ii. a second composition selected from the group consisting of glycol, glyceryl ester, and combinations thereof;
    wherein the conditioner composition comprises a gel network.
B. The hair conditioner composition of Paragraph A, wherein the conditioner composition comprises from about 0.2 wt % to about 1.5 wt % preservation system, preferably from about 0.4 wt % to about 1 wt % preservation system, more preferably from 0.5 wt % to about 0.8 wt % preservation system, and even more preferably from about 0.6 wt % to about 0.8 wt % preservation system.
C. The hair conditioner composition of Paragraphs A-B, wherein the preservation system comprises less than 2% sodium benzoate, preferably less than 1.5% sodium benzoate, more preferably less than 1% sodium benzoate, even more preferably less than 0.8% sodium benzoate, even more preferably less than 0.6 wt % sodium benzoate, and even more preferably less than 0.5% sodium benzoate.

D. The hair conditioner composition of Paragraphs A-C, wherein the preservation system comprises from about 0.1 wt % to about 0.5 wt % sodium benzoate, and preferably from about 0.2 wt % to about 0.4 wt % sodium benzoate.

E. The hair conditioner composition of Paragraphs A-D, wherein the preservation system comprises from about 20% to about 50% sodium benzoate, by weight of the preservation system, preferably from about 25% to about 50% sodium benzoate, by weight of the preservation system, more preferably about 30% to about 50% sodium benzoate, by weight of the preservation system, and even more preferably from about 30% to about 40% sodium benzoate, by weight of the preservation system.

F. The hair conditioner composition of Paragraphs A-E, wherein the preservation system comprises from about 0.3 wt % to about 1.5 wt % of a second composition, preferably from about 0.32 wt % to about 1 wt % of a second composition, more preferably from about 0.33 wt % to about 0.8 wt % of a second composition, even more preferably from about 0.34 wt % to about 0.6 wt % of a second composition, even more preferably from about 0.35 wt % to about 0.5 wt % of a second composition, even more preferably from about 0.37 wt % to about 0.45 wt % of a second composition, and even more preferably from about 0.38 wt % to about 0.43 wt % of a second composition.

G. The hair conditioner composition of Paragraphs A-F, wherein the preservation system comprises from about 50% to about 80% of the second composition, by weight of the preservation system, preferably from about 50% to about 75% of the second composition, by weight of the preservation system, more preferably from about 50% to about 70% of the second composition, by weight of the preservation system, and even more preferably from about 50% to about 67%, by weight of the preservation system.

H. The hair conditioner composition of Paragraphs A-G, wherein the second composition comprises glycol selected from the group consisting of glycols can include butylene glycol, pentylene glycol, hexylene glycol, 1,2-hexanediol, caprylyl glycol, decylene glycol, and mixtures thereof.

I. The hair conditioner composition of Paragraphs A-H, wherein the glycol comprises caprylyl glycol.

J. The hair conditioner composition of Paragraphs A-I, wherein the second composition comprises glyceryl ester selected from the group consisting of glyceryl caprylate, glyceryl caprate, glyceryl undecylenate and mixtures thereof.

K. The hair conditioner composition of Paragraphs A-J, wherein the preservation system comprises a weight ratio of sodium benzoate to the second composition from about 1:4 to about 1:1, preferably from about 1:3 to about 1:1, more preferably from about 1:2 to about 1:1, and even more preferably from about 1:1.7 to about 1:1.

L. The hair conditioner composition of Paragraphs A-K, wherein the composition comprises from about 0.1 wt % to about 10 wt % cationic surfactant, preferably from about 0.5 wt % to about 8.0 wt % cationic surfactant, and more preferably from about 0.8 wt % to about 6.0 wt % cationic surfactant.

M. The hair conditioner composition of Paragraphs A-L, wherein the cationic surfactant is selected from the group consisting of behenamidopropyl dimethylamine (BAPDMA), behentrimonium chloride, cetrimonium chloride, stearamidopropyl dimethylamine, and combinations thereof.

N. The hair conditioner composition of Paragraphs A-M, wherein the cationic surfactant comprises behenamidopropyl dimethylamine (BAPDMA).

O. The hair conditioner composition of Paragraph N, comprising from about 2 wt % to about 6.7 wt % BAPDMA, preferably from about 2.2 wt % to about 6.5 wt % BAPDMA, more preferably from about 2.5 wt % to about 6.25 wt % BAPDMA, even more preferably from about 2.75 wt % to about 6 wt % BAPDMA.

P. The hair conditioner composition of Paragraphs A-0, wherein the composition comprises from about 1 wt % to about 30 wt % high melting point fatty compound, preferably from about 1.5 wt % to about 15 wt % high melting point fatty compound, more preferably from about 2 wt % to about 8 wt %, and even more preferably from about 2.5 wt % to about 7 wt % high melting point fatty compound.

Q. The hair conditioner composition of Paragraphs A-P, where the high melting point fatty compound comprises a melting point of 25° C. or higher, preferably 40° C. or higher, more preferably 45° C. or higher, and even more preferably 49° C. or higher.

R. The hair conditioner composition of Paragraphs A-Q, wherein the high melting point fatty compound is selected from the group consisting of cetyl alcohol, stearyl alcohol, behenyl alcohol, brassica alcohol, and combinations thereof.

S. The hair conditioner composition of Paragraph R, comprising less than 8 wt % high melting point fatty compound, preferably less than 7.5 wt % high melting point fatty compound, more preferably less than 7 wt % high melting point fatty compound.

T. The hair conditioner composition of Paragraph R, comprising from about 2.5 wt % to about 9 wt % high melting point fatty compound, preferably from about 3 wt % to about 8 wt % high melting point fatty compound, more preferably from about 3.25 wt % to about 7.5 wt % high melting point fatty compound, even more preferably from about 3.5 wt % to about 7 wt % high melting point fatty compound, and even more preferably from about 4 wt % to about 6.7 wt % high melting point fatty compound.

U. The hair conditioner composition of Paragraphs A-T, wherein the conditioner composition comprises from about 40 wt % to about 99 wt % aqueous carrier, preferably from about 50 wt % to about 95 wt % aqueous carrier, more preferably from about 70 wt % to about 93 wt % aqueous carrier, and even more preferably from about 80 wt % to about 92 wt % aqueous carrier.

V. The hair conditioner composition of Paragraphs A-U, wherein the aqueous carrier comprises water.

W. The hair conditioner composition of Paragraphs A-V, wherein the level of microbes is undetectable at two days, as measured according to the Bacterial and Fungal Microbial Susceptibility Test Methods, described herein.

X. The conditioner composition of Paragraphs A-W, wherein the conditioner composition comprises a shear stress from about 50 Pa to about 500 Pa, preferably from about 75 Pa to about 450 Pa, more preferably from about 100 Pa to about 400 Pa, even more preferably from about 125 Pa to about 375 Pa, and even more preferably from about 135 Pa to about 325 Pa, as measured according to the Shear Stress Test Method, described herein.

Y. The conditioner composition of Paragraphs A-X, comprising a pH from about 2.5 to about 5, preferably from about 3.5 to about 4.5, as measured according to the pH Test Method, described herein.

Z. The hair conditioner composition of Paragraphs A-Y, wherein the composition is substantially free of, preferably free of a preservative ingredient selected from the group consisting of isothiazolinones including 5-chloro-2-methyl-4-isothiazolin-3-one and 2-methyl-4-isothiazolin-3-one (commercially available as Kathon™ CG from Dow®), benzyl alcohol, phenoxyethanol, cyclohexylglycerin, parabens, and combinations thereof.

AA. The hair conditioner composition of Paragraphs A-Z, wherein the composition is substantially free, preferably free of ethylenediaminetetraacetic acid (EDTA) and salts thereof.

BB. The hair conditioner composition of Paragraphs A-AA, wherein the composition is substantially free of, preferably free of an ingredient selected from the group consisting of silicone, propellants, phthalates, dyes, sulfates, formaldehyde donors, and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
    a) about 50% to about 95% of an aqueous carrier, by weight of the composition;
    b) about 0.1% to about 10% of a cationic surfactant, by weight of the composition;
    c) about 1.5% to about 15% of a high melting point fatty compound, by weight of the composition;
    d) a preservation system comprising:
        i) 0.2% to 0.4% sodium benzoate, by weight of the composition;
        ii) about 0.4% by weight of the composition, of a second composition selected from the group consisting of glycol, glyceryl ester, and combinations thereof;
        wherein the weight ratio of sodium benzoate to the second composition is about 1:2 to about 1:1; and
    e) a gel network,
    wherein the conditioner composition has a pH off about 2.5 to about 5, is free of anionic surfactant, and has an undetectable microbe level at two days according to the Bacterial and Fungal Microbial Susceptibility Test.

2. The hair conditioner composition of claim 1, wherein the second composition comprises a glycol selected from the group consisting of butylene glycol, pentylene glycol, hexylene glycol, 1,2-hexanediol, caprylyl glycol, decylene glycol, and mixtures thereof.

3. The hair conditioner composition of claim 1, wherein the glycol comprises caprylyl glycol.

4. The hair conditioner composition of claim 1, wherein the second composition comprises a glyceryl ester selected from the group consisting of glyceryl capiyiate, glyceryl caprate, glyceryl undecylenate and mixtures thereof.

5. The hair conditioner composition of claim 1, wherein the cationic surfactant is selected from the group consisting of behenamidopropyl dimethylamine, behentrimonium chloride, cetrimonium chloride, stearamidopropyl dimethylamine, and combinations thereof.

6. The hair conditioner composition of claim 1, wherein the high melting point fatty compound is a fatty alcohol selected from the group consisting of cetyl alcohol, stearyl alcohol, behenyl alcohol, brassica alcohol, and combinations thereof.

7. The hair conditioner composition of claim 1, wherein the conditioner composition has a shear stress off about 50 Pa to about 500 Pa, as measured according to Shear Stress Test Method.

8. The hair conditioner composition of claim 1, wherein the preservation system is substantially free of a preservative ingredient selected from the group consisting of ethylenediaminetetraacetic acid and salts thereof, isothiazolinones, benzyl alcohol, phenoxyethanol, cyclohexylglycerin, parabens, and combinations thereof.

9. The hair conditioner composition of claim 1, wherein the composition is substantially free of an ingredient selected from the group consisting of silicone, propellants, phthalates, dyes, sulfates, formaldehyde donors, and combinations thereof.

10. A hair conditioner composition that is a solid crystalline gel network comprising:
    a) about 50% to about 95% of an aqueous carrier, by weight of the composition;
    b) about 0.1 wt % to about 10 wt %, by weight of the composition, of a single cationic surfactant selected from the group consisting of behenamidopropyl dimethylamine, behentrimonium chloride, cetrimonium chloride, stearamidopropyl dimethylamine, and combinations thereof, wherein the composition is free of other surfactants;
    c) about 1.5 wt % to about 15 wt % of a fatty alcohol selected from the group consisting of cetyl alcohol, stearyl alcohol, behenyl alcohol, and brassica alcohol;

d) a preservation system comprising:
   i) about 0.2% to 0.4% sodium benzoate, by weight of the composition;
   ii) about 0.4% a glycol selected from the group consisting of butylene glycol, pentylene glycol, hexylene glycol, 1,2-hexanediol, caprylyl glycol, decylene glycol, and mixtures thereof;
      wherein the weight ratio of sodium benzoate to the glycol is about 1:2 to 1:1; and
e) a gel network,
wherein the composition has an undetectable microbe level at two days, according to the Bacterial and Fungal Microbial Susceptibility Test.

11. The hair care composition of claim 10, wherein the glycol comprises caprylyl glycol.

12. The hair care composition of claim 10, wherein the surfactant comprises behenamidopropyl dimethylamine.

13. The hair conditioner composition of claim 10, wherein microbes are undetectable at two days, as measured according to Bacterial and Fungal Microbial Susceptibility Test Methods.

* * * * *